US007550585B2

(12) United States Patent
Vonwiller et al.

(10) Patent No.: US 7,550,585 B2
(45) Date of Patent: Jun. 23, 2009

(54) SYNTHESIS OF METAL CYANINES (75) Inventors: Simone Charlotte Vonwiller, Balmain (AU); Scott Matthew Starling, Balmain (AU); Damon Donald Ridley, Balmain (AU); Lachlan Everett Hall, Balmain (AU); Simon Fielder, Balmain (AU); Graciel Gonzaga, Balmain (AU); Kia Silverbrook, Balmain (AU); Paul Lapstun, Balmain (AU)

(73) Assignee: Silverbrook Research Pty Ltd, Balmain, New South Wales (AU)

( * ) Notice: Subject to any disclaimer, the term of this patent is extended or adjusted under 35 U.S.C. 154(b) by 776 days.

(21) Appl. No.: 10/913,376

(22) Filed: Aug. 9, 2004

(65) Prior Publication Data
US 2006/0030702 A1    Feb. 9, 2006

(51) Int. Cl.
C07B 47/00 (2006.01)
(52) U.S. Cl. ..................................... 540/145
(58) Field of Classification Search .................. 540/145
See application file for complete search history.

(56) References Cited

U.S. PATENT DOCUMENTS

| 3,588,216 | A | 6/1971 | Bloom |
| 4,333,876 | A | 6/1982 | Elliott et al. |
| 4,593,113 | A | 6/1986 | Kauffman |
| 4,864,618 | A | 9/1989 | Wright et al. |
| 5,036,040 | A | 7/1991 | Chapman et al. |
| 5,051,736 | A | 9/1991 | Bennett et al. |
| 5,282,894 | A | 2/1994 | Albert et al. |
| 5,477,012 | A | 12/1995 | Sekendur |
| 5,607,762 | A | 3/1997 | Albert et al. |
| 5,652,412 | A | 7/1997 | Lazzouni et al. |
| 5,661,506 | A | 8/1997 | Lazzouni et al. |
| 5,663,326 | A | 9/1997 | Wolleb |
| 5,668,276 | A | 9/1997 | Hsiao et al. |
| 5,677,199 | A | 10/1997 | Arrhenuis |
| 5,692,073 | A | 11/1997 | Cass |
| 5,707,813 | A | 1/1998 | Dandliker et al. |
| 5,852,434 | A | 12/1998 | Sekendur |
| 6,076,734 | A | 6/2000 | Dougherty |
| 6,642,376 | B2 | 11/2003 | Lindsey et al. |
| 6,964,374 | B1 | 11/2005 | Djuknic et al. |

FOREIGN PATENT DOCUMENTS

| EP | 0266164 A2 | 5/1988 |
| EP | 0679692 B1 | 9/2001 |
| GB | 2306669 | 5/1997 |
| JP | 01-141795 A | 6/1989 |
| JP | 04146189 A | 5/1992 |
| JP | 07126561 A | 5/1995 |
| JP | 07164729 A | 6/1995 |
| JP | 07216275 A | 8/1995 |
| JP | 08073792 A | 3/1996 |
| JP | 11012425 A | 1/1999 |
| JP | 2000155439 A | 6/2000 |
| JP | 2000-191948 A | 7/2000 |
| JP | 2001-200171 A | 7/2001 |
| JP | 2001-221912 A | 8/2001 |
| JP | 2002-037968 A | 2/2002 |
| WO | WO98/32832 | * 7/1998 |
| WO | WO 98/32832 A1 | 7/1998 |
| WO | WO 99/18487 A2 | 4/1999 |
| WO | WO 99/50781 A1 | 10/1999 |
| WO | WO 02/20639 A1 | 3/2002 |
| WO | WO 02/080164 A | 10/2002 |

OTHER PUBLICATIONS

Dymetman, M., and Copperman, M., "Intelligent Paper in Electronic Publishing, Artist Imaging, and Digital Typography, Proceedings of EP '98", Mar./Apr. 1998, Springer Verlag LNCS 1375, pp. 392-406.
Asanov, A.N. et al., "Action of oxygen on thermoelectric propertieds of aluminium and tin phthacyanines substituted at the metal", Zhurnal Fizicheskoi Khimii (1982), 56 (7), 1795-6 See RN 58716-07-7 & STN File CA Abstract Accession No. 97:118939.
Baumann, ME et al., "Synthesis of axially disubstituted octakis-alkoxy germanium (IV) phthalocyanines", Proceedings of SPIE—The International Society for Optical Engineering (1994), 2078 (Photodynamic Therapy of Cancer), 460-6 See RN 156548-67-3, and RN 156548-68-4 & STN File CA Abstract Accession No. 121:77410.
Brewis, Matthew et al., "Phthalocyanine-centered and naphthalocyanine-centered aryl ether dendrimer with oligo(ethyleneoxy) surface groups", Tetrahedron (2003), 59 (22), 3863-3872 See RN 571150-95-3, and RN 571150-98-6 & STN File CA Abstract Accession No. 139:149995.
Chen, Yu et al., "New axially aryloxy substituted gallium phthalocyanines for nonlinear optics", Journal of Materials Chemistry (2003), 13 10, 2405-2408 See RN 636568-98-4 & STN File CA Abstract Accession No. 140:49833.
Chen, Yu et al., "Photophysical studies on axially substituted indium and gallium phthalocyanines upon UV-Vis laser irradiation", Solid State Communication (2004), 131 (12), 773-778 See RN 636569-001-1 & STN File CA Abstract Accession No. 141:357911.
Gross, T et al., "Investigation of rational syntheses of heteroleptic porphyrinic lanthanide (Europium, Cerium) triple-decker sandwich complexes", Inorg. Chem., vol. 40, No. 18, pp. 4762-4774 (2001).
Hartmann, Monika et al., "Polymers with the central atom of a macrocycle in the main chain. 2. Polycondensation reactions with germanium complexes of phthacyanine and meso-tetraphenylporphin", Makromolekulare Chemie (1975), 176 (4), 831-47 See RN 55948-32-8, RN 55948-33-9, RN 555948-61-3, and RN 55948-65-7 & STN File CA Abstract Accession No. 83:79670.
Huang, Jian-Dong et al., "Halogenated silicon (IV) phthacyanines with axial poly(ethylene glycol) chains. Synthesis, spectroscopic properties, complexation with bovine serum albumin and in vitro photodynamic activities", New Journal of Chemistry (2004), 28 (3), 348-354 See RN 170952-19-9, RN534603-93-5, RN 534603-94-6 & STN File CA Abstract Accession No. 141:17054 2.

(Continued)

*Primary Examiner*—James O. Wilson
*Assistant Examiner*—Paul V. Ward (57) ABSTRACT

A method for preparing a macrocyclic metal cyanine, comprising the step of providing a macrocyclic metal-free cyanine precursor and inserting a metal therein using a metal reagent, wherein said metal reagent comprises at least one organic ligand.

9 Claims, 3 Drawing Sheets

OTHER PUBLICATIONS

Ishikawa, N et al, "Determination of ligand-field parameters and f-electronic structures of hetero-dinuclear phthalocyanine complexes with a diamagnetic Yttrium(III) and a paramagnetic trivalent lanthanide ion", J. Phys. Chem. A, vol. 106, No. 41, pp. 9543-9550 (2002).

Joyner, Ralph D et al., "Germanium phthalocyanines", Journal of the American Chemical Society (1960), 82, 5790-1 See RN 55948-33-9, and RN 108127-26-0 & STN File CA Abstract Accession No. 57:34506.

Kennedy, Brendan J et al., "Spin states in iron(III) phthalocyanines studied by Moessbauer, magnetic susceptibility, and ESR measurements", Inorganic Chemistry (1986), 25 (15), 2539-45 See RN 102588-66-9 & STN File CA Abstract Accession No. 105:34539.

Kraus, Ga et al., "A convenient method for connecting aluminium phthalocyanine to phenols via the Al-O bond", Synlett (1996), (8), 726 See RN 108243-89-6, RN 182231-89-6, and RN 182231-93-2 & STN File CA Abstract Accession No. 125:264328.

Lo, Pui-Chi et al., "Preparation and photophysical properties of halogenated silicon (IV) phthalocyanines substituted axially with poly-(ethylene glycol) chains", Tetrahedron (2003), 44 (9), 1967-1970 See RN 534603-93-5, and RN 534603-94-6 & STN File CA Abstract Accession No. 139:8116.

Maree, M. David et al., "Solvent-free axial ligand substitution in octaphenoxyphthalocyaninato silicon complexes using microwave irradiation", Journal of Chemical Research, Sypnoses (2001), (2), 68-69 See RN 351345-43-2 & STN File CA Abstract Accession No. 135:146284.

Meyer, Gunter et al., "Polymers with central atom of a macrocycle in the main chanin. 3. Polycendensation reactions with tin complexes of meso-tetrahenylporphine, phthalocyanine, and hemiporphyrazine", Makromolekulare Chemie (1975). 176 (7), 1919-27 See RN 57156-38-4 & STN File CA Abstract Accession No. 83:206593.

Pan, N et al. "Templated tetramerization of dicyanobenzenes to form mixed porphyrinato and phthalocyaninato rare earth(III) triple-decker complexes", J. of Porphyrins and Phthalocyanines, vol.6, No. 5, pp. 347-357 (2002).

Rihter, BD et al., "Three new phthalocyanines with potential for PDT studies", Proceedings of SPIE—The International Society for Optical Engineering (1992), vol. 1645 (Proc. Opt. Methods Tumor Treat. Detect.: Mech. Tech. Photodyn. Ther., 1992) 251-8.

Sinha, Arun K et al., "Thin polyurethane films of polyhydroxysilicon phthalocyanine and bis-phthalocyanine derivatives", Polymer Journal (Tokyo) (1995), 27 (11) 1079-84 See RN 161729-28-8 & STN File CA Abstract Accession No. 123:341973.

Tomoda, H et al., "Synthesis of metallophthalocyanines from strong bases", Chem Lett. (1983), No. 3, pp. 313-316.

Tutass, Andreas et al., "Phthacyaninates and tetraphenylporphyrinates of high co-ordinated ZrIV/HfIV with hydoxo, chloro, (di) phenolato, (hydrogen) carbonato, and (Amino) carboxylato ligands", Zeitschrift fur Anorganische und Allgemeine Chemie (2002), 628 (5), 1027-1044 See RN 45145-64-1 & STN File CA Abstract Accession No. 137:194526.

Witkiewicz, Z et al., "Properties of octamethoxypphthalocyanines. I. On their syntheses, electrical conductivity and catalytic activity." Materials Science, vol. 2, No. 1-2, pp. 39-45 (1976).

Zhang, Qing et al., "Preparation of Langmuir-Blodgett films of phthalocyanines and investigation by atomic force microscope", Synthetic Metals (2003), 137 (1-3), 989-990 See RN 562863-52-9 & STN File CA Abstract Accession No. 139:123144.

* cited by examiner

SYNTHESIS OF METAL CYANINES

FIELD OF THE INVENTION

The present application relates to an improved method of synthesizing metal cyanines. It has been developed primarily to improve the yields for the preparation of macrocyclic metal cyanines, such as phthalocyanines and naphthalocyanines.

CO-PENDING APPLICATIONS

Various methods, systems and apparatus relating to the present invention are disclosed in the following co-pending applications filed by the applicant or assignee of the present invention simultaneously with the present application:

| | | | | |
|---|---|---|---|---|
| 7,278,727 | 10/913,373 | 10/913,374 | 10/913,372 | 7,138,391 |
| 7,153,956 | 10/913,380 | 10/913,379 | 7,122,076 | |

The disclosures of these co-pending applications are incorporated herein by cross-reference.

BACKGROUND OF THE INVENTION

Metal cyanines, such as phthalocyanines and naphthalocyanines, are excellent candidates for IR absorbing dyes. IR absorbing dyes have numerous applications, such as optical recording systems, thermal writing displays, laser filters, infrared photography, medical applications and printing. Typically, it is desirable for the dyes used in these applications to have strong absorption in the near-IR at the emission wavelengths of semiconductor lasers (e.g. between about 700 and 2000 nm, preferably between about 700 and 1000 nm). In optical recording technology, for example, gallium aluminium arsenide (GaAlAs) and indium phosphide (InP) diode lasers are widely used as light sources.

Another important application of IR dyes is in inks, such as printing inks. The storage and retrieval of digital information in printed form is particularly important. A familiar example of this technology is the use of printed, scannable bar codes. Bar codes are typically printed onto tags or labels associated with a particular product and contain information about the product, such as its identity, price etc. Bar codes are usually printed in lines of visible black ink, and detected using visible light from a scanner. The scanner typically comprises an LED or laser (e.g. a HeNe laser, which emits light at 633 nm) light source and a photocell for detecting reflected light. Black dyes suitable for use in barcode inks are described in, for example, WO03/074613.

However, in other applications of this technology (e.g. security tagging) it is desirable to have a barcode, or other intelligible marking, printed with an ink that is invisible to the unaided eye, but which can be detected under UV or IR light.

An especially important application of detectable invisible ink is in automatic identification systems, and especially "netpage" and "Hyperlabel™" systems. Netpage systems are described in the following patent applications, all of which are incorporated herein by reference.

CROSS-REFERENCES

Various methods, systems and apparatus relating to the present invention are disclosed in the following co-pending applications filed by the applicant or assignee of the present application:

| | | | | |
|---|---|---|---|---|
| 10/815,621 | 7,243,835 | 10/815,630 | 10/815,637 | 10/815,638 |
| 7,251,050 | 10/815,642 | 7,097,094 | 7,137,549 | 10/815,618 |
| 7,156,292 | 10/815,635 | 10/815,647 | 10/815,634 | 7,137,566 |
| 7,131,596 | 7,128,265 | 7,207,485 | 7,197,374 | 7,175,089 |
| 10/815,617 | 10/815,620 | 7,178,719 | 10/815,613 | 7,207,483 |
| 10/815,619 | 7,270,266 | 10/815,614 | 10/815,636 | 7,128,270 |
| 10/815,609 | 7,150,398 | 7,159,777 | 10/815,610 | 7,188,769 |
| 7,097,106 | 7,070,110 | 7,243,849 | 7,204,941 | 7,282,164 |
| 10/815,628 | 7,156,289 | 7,178,718 | 7,225,979 | 09/575,197 |
| 7,079,712 | 6,825,945 | 09/575,165 | 6,813,039 | 7,190,474 |
| 6,987,506 | 6,824,044 | 6,980,318 | 6,816,274 | 7,102,772 |
| 09/575,186 | 6,681,045 | 6,678,499 | 6,679,420 | 6,963,845 |
| 6,976,220 | 6,728,000 | 7,110,126 | 7,173,722 | 6,976,035 |
| 6,813,558 | 6,766,942 | 6,965,454 | 6,995,859 | 7,088,459 |
| 6,720,985 | 09/609,303 | 6,922,779 | 6,978,019 | 6,847,883 |
| 7,131,058 | 09/721,895 | 09/607,843 | 09/693,690 | 6,959,298 |
| 6,973,450 | 7,150,404 | 6,965,882 | 7,233,924 | 09/575,181 |
| 09/722,174 | 7,175,079 | 7,162,259 | 6,718,061 | 10/291,523 |
| 10/291,471 | 7,012,710 | 6,825,956 | 10/291,481 | 7,222,098 |
| 10/291,825 | 7,263,508 | 7,031,010 | 6,972,864 | 6,862,105 |
| 7,009,738 | 6,989,911 | 6,982,807 | 10/291,576 | 6,829,387 |
| 6,714,678 | 6,644,545 | 6,609,653 | 6,651,879 | 10/291,555 |
| 10/291,510 | 10/291,592 | 10/291,542 | 7,044,363 | 7,004,390 |
| 6,867,880 | 7,034,953 | 6,987,581 | 7,216,224 | 10/291,821 |
| 7,162,269 | 7,162,222 | 10/291,822 | 10/291,524 | 10/291,553 |
| 6,850,931 | 6,865,570 | 6,847,961 | 10/685,523 | 10/685,583 |
| 7,162,442 | 10/685,584 | 7,159,784 | 10/804,034 | 10/793,933 |
| 6,889,896 | 10/831,232 | 7,068,382 | 7,007,851 | 6,957,921 |
| 6,457,883 | 10/743,671 | 7,094,910 | 7,091,344 | 7,122,685 |
| 7,038,066 | 7,099,019 | 7,062,651 | 6,789,194 | 6,789,191 |
| 6,644,642 | 6,502,614 | 6,622,999 | 6,669,385 | 6,827,116 |
| 6,549,935 | 10/536,082 | 6,987,573 | 6,727,996 | 6,591,884 |
| 6,439,706 | 6,760,119 | 09/575,198 | 7,064,851 | 6,826,547 |
| 6,290,349 | 6,428,155 | 6,785,016 | 6,831,682 | 6,741,871 |
| 6,927,871 | 6,980,306 | 6,965,439 | 6,840,606 | 7,036,918 |
| 6,977,746 | 6,970,264 | 7,068,389 | 7,093,991 | 7,190,491 |
| 6,982,798 | 6,870,966 | 6,822,639 | 6,474,888 | 6,627,870 |
| 6,724,374 | 6,788,982 | 7,263,270 | 6,788,293 | 6,946,672 |
| 6,737,591 | 7,091,960 | 09/693,514 | 6,792,165 | 7,105,753 |
| 6,795,593 | 6,980,704 | 6,768,821 | 7,132,612 | 7,041,916 |
| 6,797,895 | 7,015,901 | 10/782,894 | 7,148,644 | 10/778,056 |
| 10/778,058 | 10/778,060 | 10/778,059 | 10/778,063 | 10/778,062 |
| 10/778,061 | 10/778,057 | 7,096,199 | 7,055,739 | 7,233,320 |
| 6,830,196 | 6,832,717 | 7,182,247 | 7,082,562 | 6,843,420 |
| 10/291,718 | 6,789,731 | 7,057,608 | 6,766,944 | 6,766,945 |
| 7,289,103 | 10/291,559 | 10/291,660 | 10/409,864 | 7,108,192 |
| 7,111,791 | 6,983,878 | 10/786,631 | 7,134,598 | 10/683,151 |
| 10/683,040 | 10/778,090 | 6,957,768 | 09/575,172 | 7,170,499 |
| 7,106,888 | 7,123,239 | 6,982,701 | 6,982,703 | 7,227,527 |
| 6,786,397 | 6,947,027 | 6,975,299 | 7,139,431 | 7,048,178 |
| 7,118,025 | 6,839,053 | 7,015,900 | 7,010,147 | 7,133,557 |
| 6,914,593 | 10/291,546 | 6,454,482 | 6,808,330 | 6,527,365 |
| 6,474,773 | 6,550,997 | 7,093,923 | 6,957,923 | 7,131,724 |

The disclosures of all of these co-pending patents/patent applications are incorporated herein by reference.

In general, the netpage system relies on the production of, and human interaction with, netpages. These are pages of text, graphics and images printed on ordinary paper, but which work like interactive web pages. Information is encoded on each page using ink which is substantially invisible to the unaided human eye. The ink, however, and thereby the coded data, can be sensed by an optically imaging pen and transmitted to the netpage system.

Active buttons and hyperlinks on each page may be clicked with the pen to request information from the network or to signal preferences to a network server. In some forms, text written by hand on a netpage may be automatically recognized and converted to computer text in the netpage system, allowing forms to be filled in. In other forms, signatures recorded on a netpage may be automatically verified, allowing e-commerce transactions to be securely authorized.

Netpages are the foundation on which a netpage network is built. They may provide a paper-based user interface to published information and interactive services.

A netpage consists of a printed page (or other surface region) invisibly tagged with references to an online description of the page. The online page description is maintained persistently by a netpage page server. The page description describes the visible layout and content of the page, including text, graphics and images. It also describes the input elements on the page, including buttons, hyperlinks, and input fields. A netpage allows markings made with a netpage pen on its surface to be simultaneously captured and processed by the netpage system.

Multiple netpages can share the same page description. However, to allow input through otherwise identical pages to be distinguished, each netpage is assigned a unique page identifier. This page ID has sufficient precision to distinguish between a very large number of netpages.

Each reference to the page description is encoded in a printed tag. The tag identifies the unique page on which it appears, and thereby indirectly identifies the page description. The tag also identifies its own position on the page.

Tags are printed in infrared-absorptive ink on any substrate which is infrared-reflective, such as ordinary paper. Near-infrared wavelengths are invisible to the human eye but are easily sensed by a solid-state image sensor with an appropriate filter.

A tag is sensed by an area image sensor in the netpage pen, and the tag data is transmitted to the netpage system via the nearest netpage printer. The pen is wireless and communicates with the netpage printer via a short-range radio link. Tags are sufficiently small and densely arranged that the pen can reliably image at least one tag even on a single click on the page. It is important that the pen recognize the page ID and position on every interaction with the page, since the interaction is stateless. Tags are error-correctably encoded to make them partially tolerant to surface damage.

The netpage page server maintains a unique page instance for each printed netpage, allowing it to maintain a distinct set of user-supplied values for input fields in the page description for each printed netpage.

Hyperlabel™ is a trade mark of Silverbrook Research Pty Ltd, Australia. In general, Hyperlabel™ systems use an invisible (e.g. infrared) tagging scheme to uniquely identify a product item. This has the significant advantage that it allows the entire surface of a product to be tagged, or a significant portion thereof, without impinging on the graphic design of the product's packaging or labeling. If the entire surface of a product is tagged ("omnitagged"), then the orientation of the product does not affect its ability to be scanned i.e. a significant part of the line-of-sight disadvantage of visible barcodes is eliminated. Furthermore, if the tags are compact and massively replicated ("omnitags"), then label damage no longer prevents scanning.

Thus, hyperlabelling consists of covering a large portion of the surface of a product with optically-readable invisible tags. When the tags utilize reflection or absorption in the infrared spectrum, they are referred to as infrared identification (IRID) tags. Each Hyperlabel™ tag uniquely identifies the product on which it appears. The tag may directly encode the product code of the item, or it may encode a surrogate ID which in turn identifies the product code via a database lookup. Each tag also optionally identifies its own position on the surface of the product item, to provide the downstream consumer benefits of netpage interactivity.

Hyperlabels™ are applied during product manufacture and/or packaging using digital printers, preferably inkjet printers. These may be add-on infrared printers, which print the tags after the text and graphics have been printed by other means, or integrated colour and infrared printers which print the tags, text and graphics simultaneously.

Hyperlabels™ can be detected using similar technology to barcodes, except using a light source having an appropriate near-IR frequency. The light source may be a laser (e.g. a GaAlAs laser, which emits light at 830 nm) or it may be an LED.

From the foregoing, it will be readily apparent that invisible IR detectable inks are an important component of netpage and Hyperlabel™ systems. In order for an IR absorbing ink to function satisfactorily in these systems, it should ideally meet a number of criteria:

(i) compatibility with inkjet printers;
(ii) compatibility of the IR dye with aqueous solvents used in inkjet inks;
(iii) intense absorption in the near infra-red region (e.g. 700 to 1000 nm);
(iv) zero or low intensity visible absorption;
(v) lightfastness;
(vi) thermal stability;
(vii) zero or low toxicity;
(viii) low-cost manufacture;
(ix) adheres well to paper and other media; and
(x) no strikethrough and minimal bleeding of the ink on printing.

Given the anticipated widespread use of netpage and Hyperlabel™ systems in the future, it is necessary to develop a high-yielding synthesis of IR absorbing dyes so that the requisite dye materials can be made readily at low cost in multigram or kilogram quantities.

As mentioned above, metal cyanines (e.g. metal phthalocyanines and metal naphthalocyanines) are an important class of dyes for netpage and Hyperlabel™ applications, since they are able to fulfil the majority of the criteria (i)-(x) above. Accordingly, it would be desirable to develop a high-yielding synthesis of metal cyanines.

The most usual synthetic approach towards metal cyanines is from macrocyclisation of aromatic vicinal dicyano compounds, although aromatic imidines may also be used as precursors. Macrocyclisation may be performed either in the presence or in the absence of a templating metal cation. A representative synthetic route to a simple metal phthalocyanine is shown below in Scheme 1. In Scheme 1, the metal is shown as "$M^{2+}$" for convenience. However, it will be readily appreciated that the metal may have any oxidation state in the phthalocyanine complex, if necessary with further ligands present.

Scheme 1

-continued

2

The metal phthalocyanine 3 may be formed directly from the dicyano compound 1 by a metal-templated base-catalysed macrocyclisation. Alternatively, the metal phthalocyanine 3 may be formed indirectly in two steps: the first step is base-catalysed macrocylisation in the absence of a templating metal to form the metal-free phthalocyanine 2; the second step is metal insertion, which converts the metal-free phthalocyanine 2 to the metallated phthalocyanine 3.

In practice either method may be conveniently used to prepare metal phthalocyanines. Whilst the one-step procedure may appear the more attractive route synthetically, this metal-templated reaction often suffers from poor yields. Accordingly, in many instances, the two-step procedure is the more efficient method for preparing metal phthalocyanines.

As mentioned above, the phthalocyanines and napthalocyanines are attractive candidates for stable IR dyes, which may be used in IR ink formulations. With the growing need for IR inks in applications such as netpage and Hyperlabel™, it would be desirable to improve the yields for the preparation of metal phthalocyanines and related macrocyclic metal cyanines.

SUMMARY OF THE INVENTION

In a first embodiment, the present invention provides a method for preparing a macrocyclic metal cyanine, comprising the step of providing a macrocyclic metal-free cyanine precursor and inserting a metal therein using a metal reagent, wherein said metal reagent comprises at least one organic ligand.

The method according to the first embdoiment advantageously improves the yield of metal insertion into macrocyclic metal-free cyanines. The present inventors have recognized the importance of the solubility of the metal reagent in the reaction medium. It has been found that the use of an organic-soluble metal reagent has a dramatic effect on the yields of metal insertion. Hence, when the metal reagent comprises one or more organic ligands, it has been found that high-yielding metal insertion reactions can be achieved. By contrast, traditional metal halide reagents (e.g. $VCl_3$) give relatively low yields (40-60%) and an apparent mixture of products.

In a second embodiment, the present invention provides a method for preparing a macrocyclic metal cyanine, comprising the step of providing an aromatic vicinal dicyano precursor or an aromatic imidine precursor and performing a templated macrocyclisation in the presence of a metal reagent, wherein said metal reagent comprises at least one organic ligand.

The method according to the second embodiment also advantageously improves the yield of macrocyclic metal cyanine synthesis. Again, the solubility of the metal reagent is understood to be a crucial factor in improving yields.

Accordingly, the present invention provides a means for improving the overall yield of the preparation of macrocyclic metal cyanines. Thus, these important IR dye compounds are made more accessible and, moreover, cheaper to manufacture.

BRIEF DESCRIPTION OF DRAWINGS

FIGS. 5(1a-d) show reflectance spectra of ink solutions comprising sulfonated vanadyl octabutoxyphthalocyanine on plain paper (80 gsm).

DETAILED DESCRIPTION OF PREFERRED FEATURES

The organic ligand may be any organic-soluble ligand, which increases the solubility of the metal reagent in the reaction medium. Examples of suitable organic ligands are acetylacetonate (acac), acetate and $C_{1-8}$ alkoxide (e.g. isopropoxide, butoxide, etc.). Metal reagents comprising such ligands are readily available commercially at relatively low cost. Examples of typical metal reagents, which may be used in the present invention are $VO(acac)_2$, $TiO(acac)_2$, $Mn(OAc)_3$, $Al(^iOPr)_3$, $Al(acac)_3$, $Sn(acac)_2Cl_2$, $Al(acac)_2OH$, $Ti(^iOPr)_4$ etc.

Preferably, the oxidation state of the metal in the metal reagent matches the oxidation state of the metal in the macrocyclic metal cyanine. Thus, if the oxidation state of the metal is, for example, +4 in the requisite metal cyanine, then the metal reagent should be selected so that the metal is also in oxidation state +4. In many instances, prior art procedures rely on adventitious oxidation of the metal under the reaction conditions to give the desired macrocyclic metal cyanine. However, the present inventors have found that relying on adventitious oxidation by, for example, atmospheric oxygen gives capricious results, with yields varying from one reaction to another and often resulting in a mixture of products. Consequently, it is important to use a metal reagent having an appropriate oxidation state.

The benefits of the present invention are especially noticeable when the metal is vanadium. Macrocyclic vanadium cyanines (e.g. vanadyl phthalocyanines) are of particular interest as IR dye compounds, because high oxidation state-vanadium (e.g. V(IV)) tends to red-shift the $\lambda_{max}$ of phthalocyanines towards wavelengths in the near-IR region. Literature procedures for forming macrocyclic vanadyl cyanines use reagents such as $VCl_3$, either as a template for macrocyclisation or for insertion into macrocyclic metal-free cyanines. However, it has been found that by using a vanadium reagent having organic ligands, the yield of cyanine formation improves dramatically.

The vanadium reagent VO(acac)$_2$ is particularly preferred in the present invention, especially when compared to traditional reagents, such as VCl$_3$. VO(acac)$_2$ is more soluble in organic solvents than VCl$_3$, which is an important factor in metal insertion and metal-templated reactions. Moreover, VO(acac)$_2$ already contains the vanadyl ("VO$^{2+}$") cation, meaning that there is no need to rely on in situ oxidation of V(III) during metal insertion or macrocyclisation. This reduces the capriciousness of the reaction and gives consistency high yields.

Preferably, the macrocyclic metal cyanine is of formula (I):

(I)

wherein

Q$^1$, Q$^2$, Q$^3$ and Q$^4$ are the same or different and are independently selected from a C$_{3-20}$ arylene group or a C$_{3-20}$ heteroarylene group;

M is selected from Si(A$^1$)(A$^2$), Ge(A$^1$)(A$^2$), Ga(A$^1$), Mg, Al(A$^1$), TiO, Ti(A$^1$)(A$^2$), ZrO, Zr(A$^1$)(A$^2$), VO, V(A$^1$)(A$^2$), Mn, Mn(A$^1$), Fe, Fe(A$^1$), Co, Ni, Cu, Zn, Sn, Sn(A$^1$)(A$^2$), Pb, Pb(A$^1$)(A$^2$), Pd and Pt;

A$^1$ and A$^2$ are axial ligands, which may be the same or different, and are selected from —OH, halogen, —OR$^3$, a hydrophilic ligand and/or a ligand suitable for reducing cofacial interactions;

R$^3$ is a selected from C$_{1-12}$ alkyl, C$_{5-12}$ aryl, C$_{5-12}$ arylalkyl or Si(R$^x$)(R$^y$)(R$^z$); and

R$^x$, R$^y$ and R$^z$ may be the same or different and are selected from C$_{1-12}$alkyl, C$_{5-12}$aryl, C$_{5-12}$ arylalkyl, C$_{1-12}$ alkoxy, C$_{5-12}$ aryloxy or C$_{5-12}$ arylalkoxy.

Q$^1$, Q$^2$, Q$^3$ and Q$^4$ may be the same or different from each other. Generally, cyanine-type dyes are symmetrical structures synthesized by a cascaded coupling of vicinal cyano groups as described above, meaning that Q$^1$, Q$^2$, Q$^3$ and Q$^4$ will have the same core structural unit. However, the method of the present invention may be used in cases where the compound is functionalized after macrocycle formation. For example, functionalization of aromatic moieties subsequent to macrocycle formation may not occur entirely symmetrically, in which case Q$^1$, Q$^2$, Q$^3$ and Q$^4$ may be different from each other by virtue of different numbers of substituent groups.

Preferably, the groups represented as Q$^1$, Q$^2$, Q$^3$ and Q$^4$ are each selected from an arylene or heteroarylene group of formula (i) to (vii) below:

(i)

(ii)

(iii)

(iv)

(v)

(vi)

or (vii)

wherein
R¹ and R² may be the same or different and are selected from hydrogen, hydroxyl, $C_{1-12}$ alkyl, $C_{1-12}$ alkyl bearing a hydrophilic or hydrophilizable group, $C_{1-12}$ alkoxy, $C_{1-12}$ alkoxy bearing a hydrophilic or hydrophilizable group, amino, $C_{1-12}$ alkylamino, di($C_{1-12}$ alkyl)amino, halogen, cyano, thiol, $C_{1-12}$ alkylthio, nitro, carboxy, $C_{1-12}$ alkylcarbonyl, $C_{1-12}$ alkoxycarbonyl, $C_{1-12}$ alklylcarbonyloxy or $C_{1-12}$ alkylcarbonylamino;
T is selected from a substituent comprising a polymeric chain or a $C_{1-30}$ hydrocarbyl group;
W is a hydrophilic group;
E is selected from —OH, —O⁻, $C_{1-12}$ alkoxy, $C_{1-16}$ alkyl, $C_{5-12}$ arylalkyl, $C_{1-6}$ alkylcarbonyl, $C_{5-12}$ arylalkylcarbonyl, $C_{1-6}$ alkoxycarbonyl or $C_{5-12}$arylalkoxycarbonyl;
m is 0, 1 or 2;
n is 0, 1 or 2; and
p is 0, 1 or 2.

Preferably, $Q^1$, $Q^2$, $Q^3$ and $Q^4$ are of formula (v).

The groups represented by R¹ and R² are primarily for modifying or "tuning" the wavelength of $\lambda_{max}$ of the dye. Electron-donating substituents (e.g. alkoxy, alkylamino) at these positions can produce a red-shift in the dye. Conversely electron-withdrawing substituents at these positions (e.g cyano, carboxy, nitro) can produce a blue-shift in the dye. By varying these substituents, the dye may be "tuned" to the frequency of a particular laser detector.

In a preferred embodiment of the present invention, R¹ and R² are both $C_{1-8}$ alkoxy groups, preferably butoxy. Butoxy substituents advantageously shift the $\lambda_{max}$ towards longer wavelengths in the near infrared, which are preferable for detection by commercially available lasers.

In an alternative preferred embodiment R¹ and R² are $C_{1-12}$ alkoxy groups bearing a hydrophilic or hydrophilizable group. $C_{1-12}$ alkoxy groups bearing a hydrophilic or hydrophilizable group are advantageous since they provide the dual functions of (i) tuning the absorption frequency of the dye, and (ii) providing hydrophilicity to aid water-dispersibility. The hydrophilic group may be a hydrophilic polymer chain; an ammonium group; an acid group including salts thereof; or a sulfonamide group, as defined above. The hydrophilizable group may be a hydroxyl, protected hydroxyl, amino, protected amino, thiol, protected thiol, cyano, ester, halogen or alkenyl group. Such groups may be readily converted into hydrophilic groups. For example, hydroxyl groups may be oxidized to carboxylic acid groups (including salts thereof); hydroxyl groups may be coupled to PEG chains; amino groups may be quaternaized using, for example, methyl iodide; thiol groups may be oxidized to sulfonic acid groups (including salts thereof) or sulfonamides; cyano and ester groups may be hydrolysed to carboxylic acid groups (including salts thereof); and alkenyl groups may be oxidatively cleaved (e.g. by ozonolysis or permanganate oxidation) to provide carboxylic acid groups (including salts thereof). In the case of protected heteroatoms, the protecting group is removed before conversion to a hydrophilic group. Hence, R¹ and R² both may be a hydroxyalkoxy group such as —O(CH₂)₄OH.

The group(s) represented by T, when present, reduces cofacial interactions between dye molecules. The suffix n in $T_n$ and the suffix p in $T_p$ indicate the number of T substituents. In cases where there are two T substituents, these may be joined to form a cyclic structure. Preferably, T is a substituent comprising a $C_{3-30}$ bridged cyclic group. Alternatively, T is a substituent comprising a polymeric chain.

The group(s) represented by W, when present, imparts hydrophilicity to the dye molecule. The suffix m in $T_m$ indicates the number of W substituents. Each of $Q^1$, $Q^2$, $Q^3$ and $Q^4$ may have different numbers of W substituents arising, for example, from unsymmetrical sulfonations. Preferably, W is selected from a substituent comprising a PEG chain; a substituent comprising an ammonium group; a substituent comprising an acid group, including salts thereof; or a substituent comprising a sulfonamide group.

An example of a hydrophilic polymeric chain is a PEG chain, which may comprise from 2 to 5000 repeating units of ethylene glycol. Other hydrophilic polymer chains will be readily apparent to the person skilled in the art. The hydrophilic polymer chain may be a substituent (or part of a substituent) on the dye molecule.

An ammonium group may be present as a substituent comprising a group of general formula —N⁺(R$^a$)(R$^b$)(R$^c$) or —U, wherein R$^a$, R$^b$, R$^c$ may be the same or different and are independently selected from H, $C_{1-8}$ alkyl (e.g. methyl, ethyl, cyclohexyl, cyclopentyl, tert-butyl, iso-propyl etc.), $C_{6-12}$ arylalkyl (e.g. benzyl, phenylethyl etc.) or $C_{6-12}$ aryl (e.g. phenyl, naphthyl etc.); and U is pyridinium, imidazolinium or pyrrolinium. Alternatively, the ammonium group may be present in the form of a quaternarized N atom in the dye molecule. For example, a heteroaromatic N atom in the dye molecule may be quaternarized with a $C_{1-8}$ alkyl or a $C_{6-12}$ arylalkyl group, in accordance with known procedures. This is shown in heteroaromatic moieties (vi) and (vii).

An acid group may be present as a substituent comprising a group of formula —CO₂Z, —SO₃Z, —OSO₃Z, –PO₃Z₂ or —OPO₃Z₂, wherein Z is H or a water-soluble cation. Preferably, Z is selected from Li⁺, Na⁺ or K⁺. Methods of introducing acid groups, such as those described above, will be well known to the person skilled in the art. For example, a carboxylic acid group may be introduced by oxidation of an olefinic or hydroxyl group in the dye molecule. Alternatively, a sulfonic acid group (–SO₃H) may be introduced to an aromatic moiety in the dye molecule by sulfonation using, for example, oleum or chlorosulfonic acid. Conversion of the acid group to its salt form can be effected using, for example, a metal hydroxide reagent (e.g. LiOH, NaOH or KOH) or a metal bicarbonate (e.g. NaHCO₃). Non-metal salts may also be prepared using, for example, an ammonium hydroxide (e.g. Bu₄NOH, NH₄OH etc.).

A sulfonamide group may be present as a substituent comprising a group of general formula —SO₂NR$^p$R$^q$, wherein R$^p$ and R$^q$ are independently selected from H, $C_{1-8}$ alkyl (e.g. methyl, ethyl, cyclohexyl, cyclopentyl, tert-butyl, iso-propyl etc.), —CH₂CH₂O)$_e$R$^e$ (wherein e is an integer from 2 to 5000 and R$^e$ is H, $C_{1-8}$ alkyl or C(O)$C_{1-8}$ alkyl), $C_{6-12}$ arylalkyl (e.g. benzyl, phenylethyl etc.) or $C_{6-12}$ aryl (e.g. phenyl, methoxyphenyl etc.).

The dye molecule prepared using the method of the present invention contains a central metal atom and preferably corresponds to a compound of formula (I). Metal-ligand dye molecules of formula (I) are preferred, since metal atoms (or ions) can be used to tune the absorption $\lambda_{max}$ of the molecule to a preferred wavelength. For example, certain metals such as Mn, V and Sn can produce large red-shifts in the $\lambda_{max}$. In this context, red-shift means a shift of $\lambda_{max}$ towards longer wavelengths as compared to the metal-free compound.

The degree of red-shift may be influenced by the oxidation state of the metal. High oxidation states (e.g. V(IV), Mn(III) and Sn(IV)) will tend to produce large red-shifts, while low oxidation states (e.g. Mn (II) and Sn(II)) will tend to produce smaller red-shifts.

The central metal atom may have one or more axial ligands, which may be introduced after macrocyclisation. Axial ligands may be used as a handle for introducing additional or supplemental functionalities into the dye molecule. Accordingly, M may be $Ti(A^1)(A^2)$, $Zr(A^1)(A^2)$, $V(A^1)(A^2)$, $Si(A^1)(A^2)$, $Ge(A^1)(A^2)$, $Ga(A^1)$, $Al(A^1)$, $Mn(A^1)$, $Fe(A^1)$, $Sn(A^1)(A^2)$, or $Pb(A^1)(A^2)$.

In cases where there are two axial ligands, these may be on opposite faces or they may be cofacial. The geometry of the ligands is generally dictated by the metal and its preferred bonding geometry.

$A^1$ and $A^2$ may be selected to add axial steric bulk to the dye molecule, thereby reducing cofacial interactions even further.

Alternatively (or in addition), $A^1$ and/or $A^2$ may be selected to add hydrophilicity to the dye molecule. Hence, $A^1$ and/or $A^2$ may include a hydrophilic group, such as any one of the groups defined as W above.

In order to introduce axial steric bulk and/or increase hydrophilicity, $A^1$ and/or $A^2$ are preferably dendrimers. In one preferred form $A^1$ and/or $A^2$ is a ligand of formula (IIIa):

(IIIa)

wherein:
$C^1$ represents a core unit having two or more branching positions;
each $P^1$ is independently selected from H, a hydrophilic moiety or a branched moiety;
$g^1$ is an integer from 2 to 8;
$q^1$ is 0 or an integer from 1 to 6;
each $p^1$ is independently selected from 0 or an integer from 1 to 6;

Preferably, the core unit $C^1$ is selected from a C atom, an N atom, a Si atom, a $C_{1-8}$ alkyl residue, a $C_{3-8}$ cycloalkyl residue, or a phenyl residue. The core unit $C^1$ has at least two branching positions, the number of branching positions corresponding to the value of $g^1$. Hence, an axial ligand having 3 branching positions and a carbon atom core (i.e. $g^1=3$; $C^1=C$ atom) may be, for example, a pentaerythritol derivative of formula (A):

(A)

Each $P^1$ group in formula (IIIa) may be the same or different. For example, in a pentaerythritol derivative (having three branching positions), there may be two arms bearing terminal hydroxyl groups ($—CH_2OH$; $P^1=H$) and one arm bearing a sulfate group ($—CH_2OSO_3Z$; $P^1=SO_3Z$).

Preferably, $P^1$ is a hydrophilic moiety. The hydrophilic moiety may be an acid group (including salts thereof), a sulfonamide group, a hydrophilic polymer chain or an ammonium group.

Accordingly, $P^1$ may comprise a hydrophilic polymer chain, such as a PEG chain. Hence, in some embodiments, $P^1$ may be of formula: $(CH_2CH_2O)_vR^6$, wherein v is an integer from 2 to 5000 (preferably 2 to 1000, preferably 2 to 100) and $R^6$ is H, $C_{1-6}$ alkyl or $C(O)C_{1-8}$ alkyl.

Alternatively, $P^1$ may comprise an acid group (including salts thereof), such as sulfonic acids, sulfates, phosphonic acids, phosphates, carboxylic acids, carboxylates etc. Hence, in some embodiments $P^1$ may be of formula: $SO_3Z$, $PO_3Z_2$, $C_{1-12}$ alkyl-$CO_2Z$, $C_{1-12}$ alkyl-$SO_3Z$ or $C_{1-12}$-alkyl-$PO_3Z_2$, $C_{1-12}$ alkyl-$OSO_{-3}Z$ or $C_{1-12}$-alkyl-$OPO_3Z_2$ wherein Z is H or a water-soluble cation. Examples of water-soluble cations are $Li^+$, $Na^+$, $K^+$, $NH_4^+$ etc.

Alternatively, $P^1$ may comprise an ammonium group, such as a quaternary ammonium group. Hence, in some embodiments $P^1$ may be of formula: $C_{1-12}$-alkyl-$N^+(R^a)(R^b)(R^c)$ or $C_{1-12}$ alkyl-U, wherein $R^a$, $R^b$, $R^c$ may be the same or different and are independently selected from H, $C_{1-8}$ alkyl (e.g. methyl, ethyl, cyclohexyl, cyclopentyl, tert-butyl, iso-propyl etc.) or $C_{6-12}$ arylalkyl (e.g. benzyl, phenylethyl etc. or $C_{6-12}$ aryl (e.g. phenyl naphthyl etc.) and U is pyridinium, imidazolinium or pyrrolinium.

Alternatively, $P^1$ may comprise a sulfonamide group, such as a group of general formula $—SO_2NR^pR^q$, wherein $R^p$ and $R^q$ are independently selected from H, $C_{1-8}$ alkyl (e.g. methyl, ethyl, cyclohexyl, cyclopentyl, tert-butyl, iso-propyl etc.), $—(CH_2CH_2O)_eR^e$ (wherein e is an integer from 2 to 5000 and $R^e$ is H, $C_{1-8}$ alkyl or $C(O)C_{1-8}$ alkyl), $C_{6-12}$ arylalkyl (e.g. benzyl, phenylethyl etc.) or $C^{1-12}$ aryl (e.g. phenyl, methoxyphenyl etc.).

Branched structures such as those described above are generally known as dendrimers. Dendrimers are advantageous since their branched chains maximize the effective three-dimensional volume of the axial ligand and, in addition, provide the potential for introducing a plurality of hydrophilic groups into the dye molecule. The pentaerythritol structure shown in formula (A) is an example of a simple dendrimer suitable for use in the present invention. Further examples are triethanolamine derivatives (B), phloroglucinol derivatives (C), and 3,5-dihydroxybenzyl alcohol derivatives (D):

In an alternative embodiment, one or more of the $P^1$ groups is itself a branched moiety. The branched moiety may be any structure adding further branching to the axial ligand, such as a moiety of formula (IIIb):

wherein:
$C^2$ represents a core unit having two or more branching positions;
$P^2$ is H or a hydrophilic moiety;
$g^2$ is an integer from 2 to 8;
$q^2$ is 0 or an integer from 1 to 6;
p2 is 0 or an integer from 1 to 6;

Preferred forms of $C^2$ and $P^2$ correspond to the preferred forms of $C^1$ and $P^1$ described above. A specific example of an axial ligand, wherein $P^1$ is a branched moiety of formala (IIIb) is dipentaerythritol derivative (E):

Alternatively, the branched moiety may comprise multiple randomized branched chains, based on motifs of core units linked by alkylene or ether chains. It will be readily understood that randomized dendrimer structures may be rapidly built up by, for example, successive etherifications of pentaerythritol with further pentaerythritol, 3,5-dihydroxybenzyl alcohol or triethanolamine moieties. One or more terminal hydroxyl groups on the dendrimer may be capped with hydrophilic groups, such as any of the hydrophilic groups above described. The extent of hydrophilic capping may be used to control the water-solubility of the dye molecule.

It will be appreciated that randomized branched structures cannot be readily illustrated using precise structural formulae. However, all branched dendrimer-like structures are contemplated within the scope of the above definitions of $A^1$ and $A^2$.

The term "hydrocarbyl" is used herein to refer to monovalent groups consisting generally of carbon and hydrogen. Hydrocarbyl groups thus include alkyl, alkenyl and alkynyl groups (in both straight and branched chain forms), carbocyclic groups (including polycycloalkyl groups such as bicyclooctyl and adamantyl) and aryl groups, and combinations of the foregoing, such as alkylcycloalkyl, alkylpolycycloalkyl, alkylaryl, alkenylaryl, alkynylaryl, cycloalkylaryl and cycloalkenylaryl groups. Similarly, the term "hydrocarbylene" refers to divalent groups corresponding to the monovalent hydrocarbyl groups described above.

Unless specifically stated otherwise, up to four —C—C— and/or —C—H moieties in the hydrocarbyl group may be optionally interrupted by one or more moieties selected from —O—; —NR$_w$—; —S—; —C(O)—; —C(O)O—; —C(O)NR$^w$—; —S(O)—; —SO$_2$—; —SO$_2$—; —SO$_2$NR$^w$; where $R^w$ is a group selected from H, $C_{1-12}$ alkyl, $C_{6-12}$ aryl or $C_{6-12}$ arylalkyl.

Unless specifically stated otherwise, where the hydrocarbyl group contains one or more —C=C— moieties, up to four —C=C— moieties may optionally be replaced by —C=N—. Hence, the term "hydrocarbyl" may include moieties such as heteroaryl, ether, thioether, carboxy, hydroxyl, alkoxy, amine, thiol, amide, ester, ketone, sulfoxide, sulfonate, sulfonamide etc.

Unless specifically stated otherwise, the hydrocarbyl group may comprise up to four substituents independently selected from halogen, cyano, nitro, a hydrophilic group as defined above (e.g. —SO$_3$H, —SO$_3$K, —CO$_2$Na, —NH$_3^+$, —NMe$_3^+$ etc.) or a polymeric group as defined above (e.g. a polymeric group derived from polyethylene glycol).

As used herein, the term "bridged cyclic group" includes $C_{4-30}$ carbocycles (preferably $C_{6-20}$ carbocycles) containing 1, 2, 3 or 4 bridging atoms. Examples of bridged carbocyclic groups are bornyl and triptycenyl, and derivatives thereof. The term "bridged cyclic group" also includes bridged polycyclic groups, including groups such as adamantanyl and tricyclo[5.2.1.0]decanyl, and derivatives thereof.

Unless specifically stated otherwise, the term "bridged cyclic group" also includes bridged carbocycles wherein 1, 2, 3 or 4 carbon atoms are replaced by heteroatoms selected from N, S or O (i.e. bridged heterocycles). When it is stated that a carbon atom in a carbocycle is replaced by a heteroatom, what is meant is that —CH— is replaced by —N—, —CH$_2$— is replaced by —O—, or —CH$_2$— is replaced by —S—. Hence, the term "bridged cyclic group" includes bridged heterocyclic groups, such as quinuclidinyl and tropanyl. Unless specifically stated otherwise, any of the bridged cyclic groups may be optionally substituted with 1, 2, 3 or 4 of the substituents described below.

The term "aryl" is used herein to refer to an aromatic group, such as phenyl, naphthyl or triptycenyl. $C_{6-12}$ aryl, for example, refers to an aromatic group having from 6 to 12 carbon atoms, excluding any substituents. The term "arylene", of course, refers to divalent groups corresponding to the monovalent aryl groups described above. Any reference to aryl implicitly includes arylene, where appropriate.

The term "heteroaryl" refers to an aryl group, where 1, 2, 3 or 4 carbon atoms are replaced by a heteroatom selected from N, O or S. Examples of heteroaryl (or heteroaromatic) groups include pyridyl, benzimidazolyl, indazolyl, quinolinyl, isoquinolinyl, indolinyl, isoindolinyl, indolyl, isoindolyl, furanyl, thiophenyl, pyrrolyl, thiazolyl, imidazolyl, oxazolyl, isoxazolyl, pyrazolyl, isoxazolonyl, piperazinyl, pyrimidinyl, piperidinyl, morpholinyl, pyrrolidinyl, isothiazolyl, triazolyl, oxadiazolyl, thiadiazolyl, pyridyl, pyrimidinyl, benzopyrimidinyl, benzotriazole, quinoxalinyl, pyridazyl, coumarinyl etc. The term "heteroarylene", of course, refers to divalent groups corresponding to the monovalent heteroaryl groups described above. Any reference to heteroaryl implicitly includes heteroarylene, where appropriate.

Unless specifically stated otherwise, aryl, arylene, heteroaryl and heteroarylene groups may be optionally substituted with 1, 2, 3, 4 or 5 of the substituents described below.

Where reference is made to optionally substituted groups (e.g. in connection with bridged cyclic groups, aryl groups or heteroaryl groups), the optional substituent(s) are independently selected from $C_{1-8}$ alkyl, $C_{1-8}$ alkoxy, —$(OCH_2CH_2)_dOR^d$ (wherein d is an integer from 2 to 5000 and $R^d$ is H, $C_{1-8}$ alkyl or $C(O)C_{1-8}$ alkyl), cyano, halogen, amino, hydroxyl, thiol, —$SR^v$, —$NR^uR^v$, nitro, phenyl, phenoxy, —$CO_2R^v$, —$C(O)R^v$, —$OCOR^v$, —$SO_2R^v$, —$OSO_2R^v$, —$SO_2OR^v$, —$NHC(O)R^v$, —$CONR^uR^v$, —$CONR^uR^v$, —$SO_2NR^uR^v$, wherein $R^u$ and $R^v$ are independently selected from hydrogen, $C_{1-12}$ alkyl, phenyl or phenyl-$C_{1-8}$ alkyl (e.g. benzyl). Where, for example, a group contains more than one substituent, different substituents can have different $R^u$ or $R^v$ groups. For example, a naphthyl group may be substituted with three substituents: —$SO_2NHPh$, —$CO_2Me$ group and —$NH_2$.

The term "alkyl" is used herein to refer to alkyl groups in both straight and branched forms. Unless stated otherwise, the alkyl group may be interrupted with 1, 2 or 3 heteroatoms selected from O, N or S. Unless stated otherwise, the alkyl group may also be interrupted with 1, 2 or 3 double and/or triple bonds. However, the term "alkyl" usually refers to alkyl groups having no heteroatom interruptions or double or triple bond interruptions. Where "alkenyl" groups are specifically mentioned, this is not intended to be construed as a limitation on the definition of "alkyl" above.

Where reference is made to, for example, $C_{1-12}$ alkyl, it is meant the alkyl group may contain any number of carbon atoms between 1 and 12. Unless specifically stated otherwise, any reference to "alkyl" means $C_{1-12}$ alkyl, preferably $C_{1-6}$ alkyl.

The term "alkyl" also includes cycloalkyl groups. As used herein, the term "cycloalkyl" includes cycloalkyl, polycycloalkyl, and cycloalkenyl groups, as well as combinations of these with linear alkyl groups, such as cycloalkylalkyl groups. The cycloalkyl group may be interrupted with 1, 2 or 3 heteroatoms selected from O, N or S. However, the term "cycloalkyl" usually refers to cycloalkyl groups having no heteroatom interruptions. Examples of cycloalkyl groups include cyclopentyl, cyclohexyl, cyclohexenyl, cyclohexylmethyl and adamantyl groups.

The term "arylalkyl" refers to groups such as benzyl, phenylethyl and naphthylmethyl.

The term "halogen" or "halo" is used herein to refer to any of fluorine, chlorine, bromine and iodine. Usually, however, halogen refers to chlorine or fluorine substituents.

Where reference is made to "a substituent comprising..." (e.g. "a substituent comprising a hydrophilic group", "a substituent comprising an acid group (including salts thereof)", "a substituent comprising a polymeric chain" etc.), the substituent in question may consist entirely or partially of the group specified. For example, "a substituent comprising an acid group (including salts thereof)" may be of formula —$(CH_2)_j$—$SO_3K$, wherein j is 0 or an integer from 1 to 6. Hence, in this context, the term "substituent" may be, for example, an alkyl group, which has a specified group attached. However, it will be readily appreciated that the exact nature of the substituent is not crucial to the desired functionality, provided that the specified group is present.

Chiral compounds described herein have not been given stereo-descriptors. However, when compounds may exist in stereoisomeric forms, then all possible stereoisomers and mixtures thereof are included (e.g. enantiomers, diastereomers and all combinations including racemic mixtures etc.).

Likewise, when compounds may exist in a number of regioisomeric forms, then all possible regioisomers and mixtures thereof are included.

For the avoidance of doubt, the term "a" (or "an"), in phrases such as "comprising a", means "at least one" and not "one and only one". Where the term "at least one" is specifically used, this should not be construed as having a limitation on the definition of "a".

Throughout the specification, the term "comprising", or variations such as "comprise" or "comprises", should be construed as including a stated element, integer or step, but not excluding any other element, integer or step.

The invention will now be described with reference to the following drawings and examples. However, it will of course be appreciated that this invention may be embodied in many other forms without departing from the scope of the invention, as defined in the accompanying claims.

EXAMPLES

In the following examples, uv-visible spectra are reported conventionally by stating an absorption wavelength first, followed by the corresponding log $\epsilon_{max}$ in parentheses. For example, "760 (5.11)" denotes an absorption at 760 nm having a log $\epsilon_{max}$ of 5.11.

(a) Metal free phthalocyanine—H₂Pc(dib)₄(OBu)₈

Figure 1:
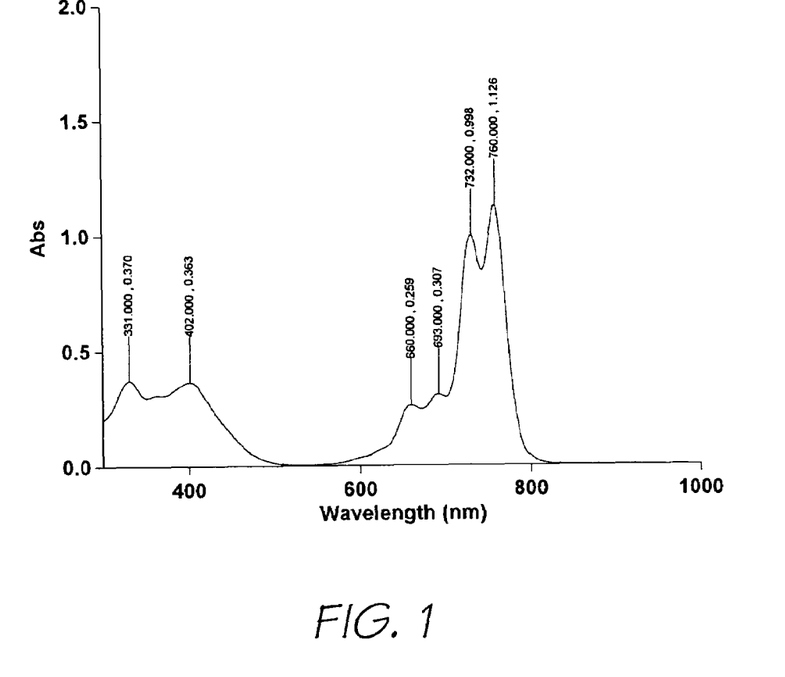
FIG. 1 shows an absorption spectrum of a metal-free phthalocyanine prepared in (a).

Lithium metal (78.2 mg; 11 mmol) was added portionwise to a boiling solution of the phthalonitrile (203 mg; 0.49 mmol) in n-butanol (10 mL). After 45 min the reaction mixture was cooled, and diluted with water (20 mL) and acetic acid (5 mL). The dark mixture was poured into water (200 mL) and extracted with chloroform (3×150 mL). The combined extracts were dried (Na₂SO₄) and the solvents were removed under high vacuum. The crude phthalocyanine was purified by column chromatography [alumina (activity grade I), toluene] to give the pure product as an apple-green powder (90 mg; 47%). $\lambda_{max}$ 760 (5.11), 732 (5.07), 693 (4.54), 660 (4.48), 402 (4.61), 331 (4.62); $^1$H NMR spectrum (CDCl₃) δ−0.20 (2H, s, NH), 1.16 (24H, t, J=7.3 Hz, 8×CH₃), 1.69 (16H, sxt, J=7.3 Hz, 8×CH₂), 2.20 (16H, qnt, J=7.3 Hz, 8×CH₂), 4.93 (16H, t, J=7.3 Hz, 8×CH₂O), 6.50 (8H, x, 8×CH), 7.10-7.13 (16H, m, Ar—H), 7.63-7.65 (16H, m, Ar—H).

(b) Vanadyl octabutoxyphthalocyanine

Example 1

Figure 2:
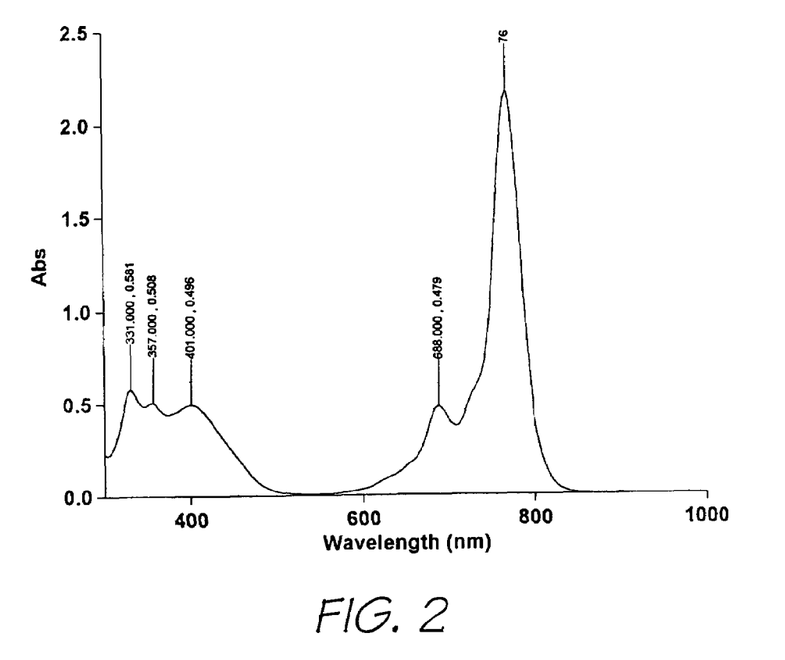
FIG. 2 shows an absorption spectrum of a vanadyl octabutoxyphthalocyanine prepared in Example 1.

VO(acac)₂ metal insertion $H_2Pc(dib)_4(OBu)_8$ (113 mg; 0.071 mmol) was suspended in dry DMF (5 mL) and then vanadyl acetylacetonate (97 mg; 0.37 mmol) and tributylamine (500 μL) were added consecutively with stirring. The resulting mixture was heated under reflux overnight, cooled and diluted with dichloromethane (200 mL). The solution was washed with water (100 mL), HCl (0.1 M; 2×100 mL) and saturated $NaHCO_3$ (100 mL), and dried ($MgSO_4$). Removal of the solvent left a dark green solid that was dissolved in toluene and purified by column chromatography on neutral alumina (toluene). The first green band contained the product and removal of the solvent afforded a green powder (90 mg; 76%). $^1$H NMR ($CDCl_3$) (all signals are broad) δ1.15-1.26; 1.67-1.76; 2.1-2.4; 4.9-5.0; 6.4-6.7; 7.10-7.23; 7.64-7.70; $\lambda_{max}$ 768 (5.2), 688 (4.6), 401 (4.6), 357 (4.6), 331 (4.7) nm.

Comparative Example 1

$VCl_3$ templated macrocyclisation

Figure 3:
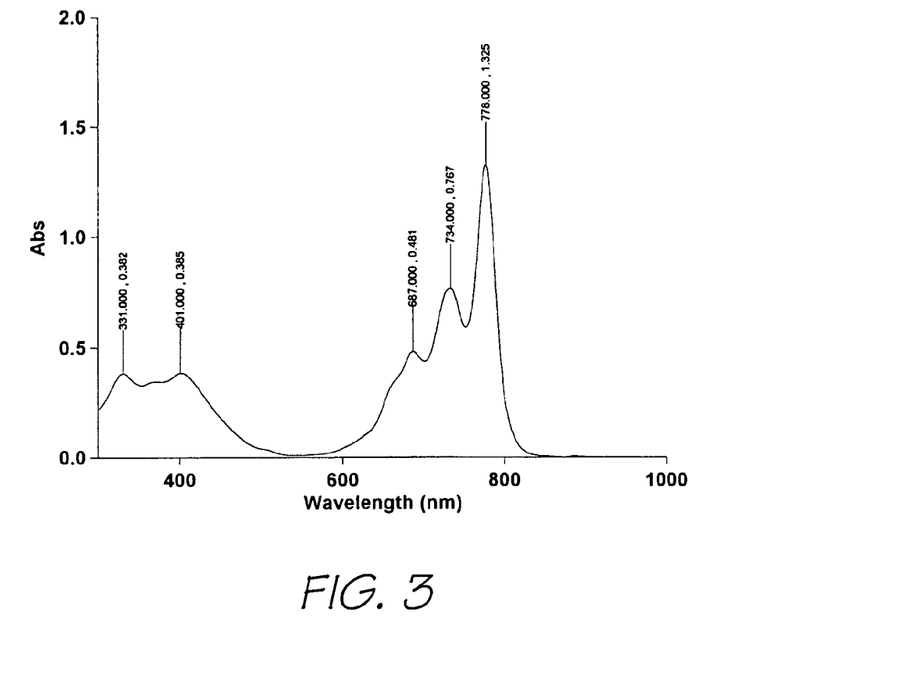
FIG. 3 shows an absorption spectrum of a vanadyl octabutoxyphthalocyanine mixture prepared in Comparative Example 1.

Lithium metal (157 mg; 23 mmol) was added portionwise to a boiling solution of the phthalonitrile (689 mg; 1.6 mmol) and vanadium(III) chloride (108 mg; 0.70 mmol) in n-BuOH (20 mL). After 1 h under reflux, the reaction mixture was cooled, diluted with dichloromethane (100 mL) and poured into water (100 mL). After shaking a separating the layers, the aqueous layer was extracted with dichloromethane (100 mL), the combined organic layers were dried (MgSO$_4$) and the solvent removed under high vacuum. The crude product was purified by column chromatography [alumina (activity grade 1), toluene] followed by trituration in warm hexane and filtration to give the vanadium phthalocyanine as a green powder (286 mg; 42%) and as a mixture of up to four vanadium species, possible comprising oxovanadium, chlorovanadium and butoxyvanadium species. $\lambda_{max}$ 778 (5.11), 734 (4.88), 687 (4.67), 401 (4.57), 331 (4.57).

(c) Sulfonation of VOPc(dib)$_4$(OBu)$_8$ to VOPc(dib)$_4$(OBu)$_8$S$_8$

Figure 4:
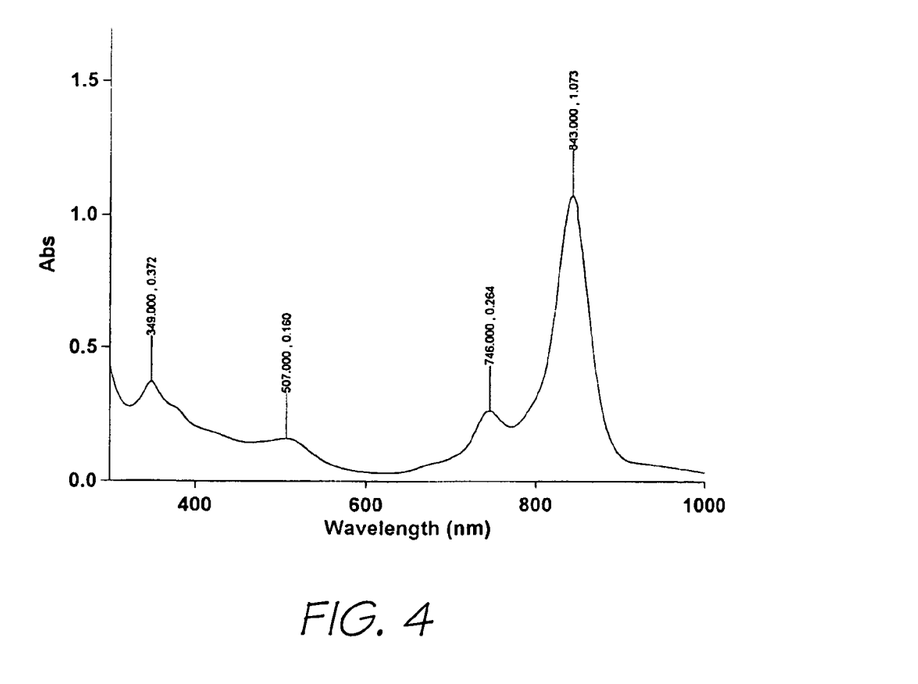
FIG. 4 shows an absorption spectrum of a sulfonated vanadyl octabutoxyphthalocyanine prepared in (c).
Figure 5:
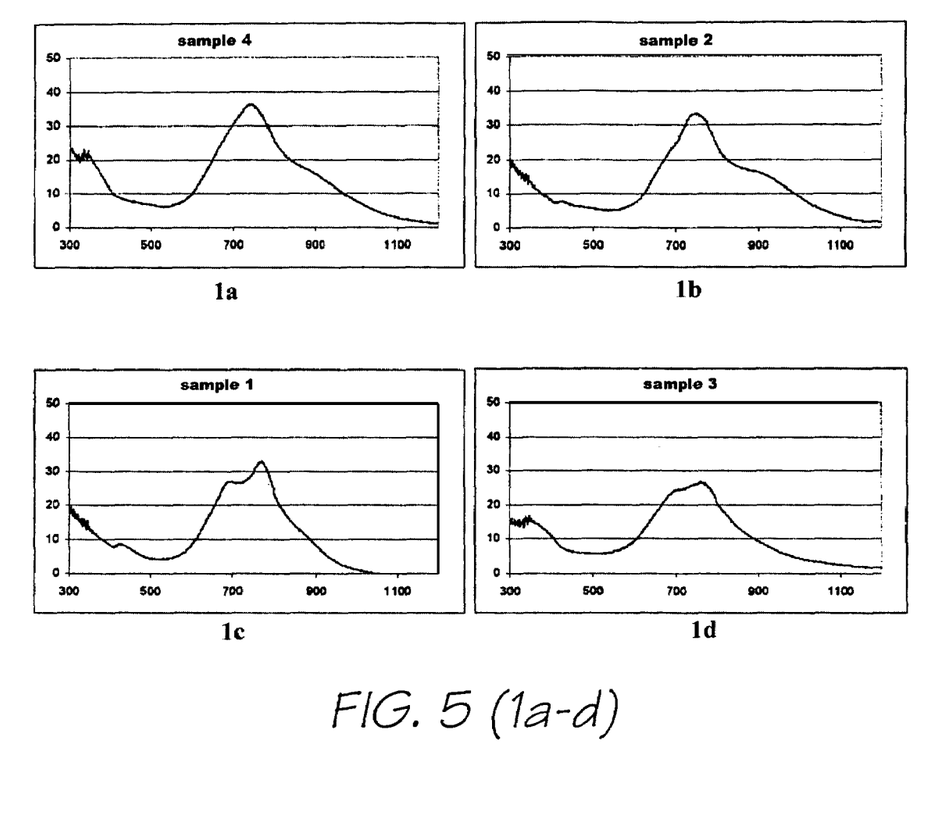

VOPc(dib)$_4$(OBu)$_8$ (22.7 mg; 13.7 μmol) in oleum (1.5 mL) was stirred at room temperature for 1 h. The deep blue solution containing the sulfonated derivative (presumed to be VOPc(dib)$_4$(OBu)$_8$S$_8$) was first analysed by taking an aliquot and diluting it in DMSO to give a 10 μM solution. The resulting purple solution had $\lambda_{max}$ 843, 746 nm. The remainder of the reaction solution was quenched by carefully adding it to ice (5 g) and washing with sulfuric acid (98%, 0.5 mL) giving a total volume of 6 mL. Aliquots (4×1 mL) of this solution were diluted to 5 mL with either water (2× samples) or ink-base (2× samples). One of each pair of samples was neutralised with solid NaHCO$_3$ to pH 7-8 while the other samples remained acidic (Table 1). The final concentration of each sample was ca. 4 mg in 5 mL (ca. 0.1% w/v). Each solution was applied to plain paper (80 gsm) with a brush and reflectance spectra were recorded on a Cary 5E spectrometer with an integrating sphere.

TABLE 1

Composition of ink-base

| ingredient | Concentration (v/v) |
| --- | --- |
| Polyethylene glycol 400 | 9.0% |
| 1,2-hexanediol | 6.0% |
| glycerol | 6.0% |
| triethylene glycol monomethyl ether | 2.0% |
| triethylene glycol | 1.0% |
| Surfynol ® surfactant | 0.5% |
| 0.01 M acetic acid | 74.5% |

TABLE 2

Test solutions for reflectance vis-NIR spectroscopy

| sample | medium | additive | pH |
| --- | --- | --- | --- |
| 1 | Water | None | <2 |
| 2 | Water | NaHCO$_3$ | 7-8 |
| 3 | Ink-base | None | <2 |
| 4 | Ink-base | NaHCO$_3$ | 7-8 |

The invention claimed is:

1. A method for preparing a macrocyclic metal cyanine, comprising the step of providing a macrocyclic metal-free cyanine compound and inserting a metal therein using a metal reagent, wherein said metal reagent comprises at least one organic ligand, wherein said organic ligand is acetylacetonate (acac), acetate or $C_{1-8}$ alkoxide, and wherein the macrocyclic metal cyanine is of formula (I):

(I)

wherein
$Q^1$, $Q^2$, $Q^3$ and $Q^4$ are the same or different and are independently selected from a $C_{3-20}$ arylene group or a $C_{3-20}$ heteroarylene group;
M is selected from Si(A$^1$)(A$^2$), Ge(A$^1$)(A$^2$), Ga(A$^1$), Mg, Al(A$^1$), TiO, Ti(A$^1$)(A$^2$), ZrO, Zr(A$^1$)(A$^2$), VO, V(A$^1$)(A$^2$), Mn, Mn(A$^1$), Fe, Fe(A$^1$), Co, Ni, Cu, Zn, Sn, Sn(A$^1$)(A$^2$), Pb, Pb(A$^1$)(A$^2$), Pd and Pt;
$A^1$ and $A^2$ are axial ligands, which may be the same or different, and are selected from —OH, halogen, —OR$^3$, a hydrophilic ligand and/or a ligand suitable for reducing cofacial interactions;
$R^3$ is a selected from $C_{1-12}$ alkyl, $C_{5-12}$ aryl, $C_{5-12}$ arylalkyl or Si(R$^x$)(R$^y$)(R$^z$); and
$R^x$, $R^y$ and $R^z$ may be the same or different and are selected from $C_{1-12}$ alkyl, $C_{5-12}$ aryl, $C_{5-12}$ arylalkyl, $C_{1-12}$ alkoxy, $C_{5-12}$ aryloxy or $C_{5-12}$ arylalkoxy.

2. The method of claim 1, wherein the oxidation state of the metal in said metal reagent matches the oxidation state of the metal in said macrocyclic metal cyanine.

3. The method of claim 1, wherein the metal is vanadium.

4. The method of claim 1, wherein the metal reagent is VO(acac)$_2$.

5. The method of claim 1, wherein $Q^1$, $Q^2$, $Q^3$ and $Q^4$ are selected from an arylene or heteroarylene group of the formula:

(i)

(ii)

(iii)

(iv)

(v)

wherein

R$^1$ and R$^2$ may be the same or different and are selected from hydrogen, hydroxyl, C$_{1-12}$ alkyl, C$_{1-12}$ alkyl bearing a hydrophilic or hydrophilizable group, C$_{1-12}$ alkoxy, C$_{1-12}$ alkoxy bearing a hydrophilic or hydrophilizable group, amino, C$_{1-12}$ alkylamino, di(C$_{1-12}$ alkyl)amino, halogen, cyano, thiol, C$_{1-12}$ alkylthio, nitro, carboxy, C$_{1-12}$ alkylcarbonyl, C$_{1-12}$ alkoxycarbonyl, C$_{1-12}$ alkylcarbonyloxy or C$_{1-12}$ alkylcarbonylamino;

T is selected from a substituent comprising a polymeric chain or a C$_{1-30}$ hydrocarbyl group;

W is a hydrophilic group;

E is selected from —OH, —O$^-$, C$_{1-12}$ alkoxy, C$_{1-6}$ alkyl, C$_{5-12}$ arylalkyl, C$_{1-6}$ alkylcarbonyl, C$_{5-12}$ arylalkylcarbonyl, C$_{1-6}$ alkoxycarbonyl or C$_{5-12}$ arylalkoxycarbonyl;

m is 0, 1 or 2;

n is 0, 1 or 2; and p is 0, 1 or 2.

6. The method of claim 5, wherein R$^1$ and R$^2$ are selected from hydrogen or C$_{1-8}$ alkoxy.

7. The method of claim 5, wherein W is selected from a substituent comprising a PEG chain; a substituent comprising an ammonium group; a substituent comprising an acid group, including salts thereof or a substituent comprising a sulfonamide group.

8. The method of claim 5, wherein W is —SO$_3$H or a water-soluble salt thereof.

9. The method of claim 5, wherein M is Ti(A$^1$)(A$^2$), Zr(A$^1$)(A$^2$), V(A$^1$)(A$^2$), Si(A$^1$)(A$^2$), Ge(A$^1$)(A$^2$), Ga(A$^1$), Al(A$^1$), Mn(A$^1$), Fe(A$^1$), Sn(A$^1$)(A$^2$), or Pb(A$^1$)(A$^2$).

* * * * *